United States Patent
Takahashi

(10) Patent No.: US 9,989,475 B2
(45) Date of Patent: Jun. 5, 2018

(54) METHOD FOR AUTOMATICALLY MEASURING CONCENTRATION OF DISSOLVED SUBSTANCE

(71) Applicant: KURITA WATER INDUSTRIES LTD., Nakano-ku, Tokyo (JP)

(72) Inventor: Junichi Takahashi, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 0 days. days.

(21) Appl. No.: 15/206,822

(22) Filed: Jul. 11, 2016

(65) Prior Publication Data

US 2016/0320309 A1 Nov. 3, 2016

Related U.S. Application Data

(63) Continuation of application No. 14/440,523, filed as application No. PCT/JP2013/078134 on Oct. 17, 2013.

(30) Foreign Application Priority Data

Nov. 6, 2012 (JP) .................................. 2012-244753
Oct. 3, 2013 (JP) .................................. 2013-207840

(51) Int. Cl.
G01N 21/80 (2006.01)
G01N 21/85 (2006.01)
G01N 21/78 (2006.01)

(52) U.S. Cl.
CPC ............. G01N 21/80 (2013.01); G01N 21/85 (2013.01); *G01N 21/78* (2013.01)

(58) Field of Classification Search
CPC ......... G01N 21/80; G01N 21/78; G01N 21/85
See application file for complete search history.

(56) References Cited

U.S. PATENT DOCUMENTS 6,774,992 B1 * 8/2004 Garver ................. D21C 9/1052
356/301

\* cited by examiner

*Primary Examiner* — Dennis White
*Assistant Examiner* — Bryan Kilpatrick
(74) *Attorney, Agent, or Firm* — Manabu Kanesaka

(57) ABSTRACT

In measuring a dissolved substance, a concentration of a specific dissolved substance in a sample water is measured using a measuring water W1 developing a specific color within a specific pH range by adding each of two reagents to a sample water W0, and an acid-base indicator S developing different colors other than the specific color is selected in a first pH range including the specific pH range and a second pH range deviating from the first pH range. Next, a reagent is prepared by adding the acid-base indicator to one reagent wherein a pH value of a reagent added water where the two kinds of reagents are separately added to the sample water is within the second pH range. Next, absorbance values are calculated by three region component lights which are a transmitted light in the measuring water wherein the prepared reagent is added.

2 Claims, 9 Drawing Sheets

FIG. 5

| Data No | Case | Free residual chlorine concentration (mg/L) | Reagent addition concentration (mg/10mL) | | Value of absorbances | | | Presence or absence of selected indicator | Criterion formula (1) related to value of 2Ba−Ga |
|---|---|---|---|---|---|---|---|---|---|
| | | | First reagent (Buffer solution) | Second reagent | R Region component light $R_a$ | G Region component light $G_a$ | B Region component light $B_a$ | | |
| 1 | Preparing water | 0.0 | 0 | 0 | 0.00 | 0.00 | 0.00 | — | 0.00 |
| 2 | Case without indicator | 0.0 | 0.2 | 0.2 | 0.00 | 0.00 | 0.00 | Absence | 0.00 |
| 3 | | 0.6 | 0.2 | 0.2 | 0.01 | 0.17 | 0.11 | Absence | 0.05 |
| 4 | | 1.1 | 0.2 | 0.2 | 0.02 | 0.33 | 0.18 | Absence | 0.03 |
| 5 | | 1.6 | 0.2 | 0.2 | 0.02 | 0.44 | 0.22 | Absence | 0.00 |
| 6 | | 2.0 | 0.2 | 0.2 | 0.03 | 0.55 | 0.27 | Absence | −0.01 |
| 7 | Case with indicator | 0.0 | 0.2 | 0.2 | 0.02 | 0.08 | 0.22 | Presence | 0.36 |
| 8 | | 0.6 | 0.2 | 0.2 | 0.03 | 0.23 | 0.30 | Presence | 0.37 |
| 9 | | 1.1 | 0.2 | 0.2 | 0.03 | 0.37 | 0.36 | Presence | 0.35 |
| 10 | | 1.6 | 0.2 | 0.2 | 0.03 | 0.48 | 0.40 | Presence | 0.32 |
| 11 | | 2.0 | 0.2 | 0.2 | 0.03 | 0.60 | 0.46 | Presence | 0.32 |
| 12 | Case without adding first reagent | 0.0 | 0 | 0.2 | 0.00 | 0.00 | 0.01 | Presence | 0.01 |
| 13 | | 0.6 | 0 | 0.2 | 0.02 | 0.19 | 0.11 | Presence | 0.03 |
| 14 | | 1.1 | 0 | 0.2 | 0.03 | 0.34 | 0.18 | Presence | 0.03 |
| 15 | | 1.6 | 0 | 0.2 | 0.02 | 0.41 | 0.23 | Presence | 0.06 |
| 16 | | 2.0 | 0 | 0.2 | 0.03 | 0.44 | 0.26 | Presence | 0.08 |
| 17 | Case without adding second reagent | 0.0 | 0.2 | 0 | 0.44 | 0.41 | 0.10 | Presence | −0.22 |
| 18 | | 0.6 | 0.2 | 0 | 0.45 | 0.42 | 0.09 | Presence | −0.23 |
| 19 | | 1.1 | 0.2 | 0 | 0.42 | 0.39 | 0.10 | Presence | −0.19 |
| 20 | | 1.6 | 0.2 | 0 | 0.46 | 0.43 | 0.09 | Presence | −0.25 |
| 21 | | 2.0 | 0.2 | 0 | 0.40 | 0.34 | 0.08 | Presence | −0.19 |

| Step of judging presence or absence of addition of reagents Case wherein selected indicator is added to first reagent and second reagent ||| 
|---|---|---|
| Condition of addition of reagents | Condition of color development of measuring water | Judgement |
| Both first reagent and second reagent are added. | Specific color is developed by dissolved substance.<br>Also, first color is developed deeply (strongly) by selected indicator of first reagent and second reagent. | Developing deep (strong) first color<br>Specifically, just have to satisfy criterion formula (3) |
| Only one of first reagent or second reagent is added. | pH value of measuring water: First pH range<br>First color is developed by selected indicator.<br>pH value of measuring water: Second pH range<br>Second color is developed by selected indicator.<br>pH value of measuring water: Color change region<br>Intermediate color between first color and second color is developed by selected indicator. | Developing no deep (strong) first color<br>Specifically, not satisfying criterion formula (3) |
| Both first reagent and second reagent are added.<br>Since pH value of sample water is unusual, pH value of measuring water is within second pH range. | Specific color is developed by dissolved substance.<br>Also, second color is developed deeply (strongly) by selected indicatoe of first reagent and second reagent. | Developing deep (strong) second color |
| Note: Criterion formulas are in a case wherein dissolved substance is phosphate ion. |||

| Step of judging presence or absence of addition of reagents Case wherein selected indicator is added to first reagent and coloring agent is added to second reagent ||| 
|---|---|---|
| Condition of addition of reagents | Condition of color development of measuring water | Judgement |
| Both first reagent and second reagent are added. | Specific color is developed by dissolved substance. Also, first color is developed deeply (strongly) by selected indicator and coloring agent. | Developing deep (strong) first color Specifically, satisfying criterion formula (3) |
| Only one of first reagent or second reagent is added. | pH value of measuring water: First pH range First color is developed by selected indicator or coloring agent. pH value of measuring water: Second pH range Second color is developed by selected indicator, or first color is developed by coloring agent. pH value of measuring water: Color chage region Intermediate color between first color and second color is developed by selected indicator, or first color is developed by coloring agent. | Developing no deep (strong) first color Specifically, not satisfying criterion formula (3) |
| Both first reagent and second reagent are added. Since pH value of sample water is unusual, pH value of measuring water is within second pH range. | Specific color is developed by dissolved substance. Also, second color is developed by selected indicator of first reagent, and first color is developed by coloring agent of second reagent. | |
| Only one of first reagent or second reagent is added. Since pH value of sample water is unusual, pH value of measuring water is within second pH range. | Second color is developed by selected indicator of first reagent, or first color is developed by coloring agent of second reagent. | |
| Note: Criterion formulas is in a case wherein dissolved substance is phosphate ion. |||

FIG. 9

| Data No | Case | Phosphate ion concentration (mg/L) | Reagent addition concentration (mg/10mL) | | Value of absorbances | | | Presence or absence of coloring agent | Criterion formula (3) related to value of Ba - 0.34Ra | Criterion formula (4) related to value of Ga - 0.66Ra | pH of measuring water and the like |
|---|---|---|---|---|---|---|---|---|---|---|---|
| | | | First reagent | Second reagent | R Region component light Ra | G Region component light Ga | B Region component light Ba | | | | |
| 1 | Preparing water | 0.0 | 0 | 0 | 0.00 | 0.00 | 0.00 | — | 0.00 | 0.00 | Neutrality |
| 2 | Case without coloring agent | 0.0 | 0.2 | 0.2 | 0.00 | 0.00 | 0.00 | Absence | 0.00 | 0.00 | pH < 6.8 |
| 3 | | 1.0 | 0.2 | 0.2 | 0.07 | 0.04 | 0.02 | Absence | 0.00 | -0.01 | pH < 6.8 |
| 4 | | 2.0 | 0.2 | 0.2 | 0.15 | 0.09 | 0.05 | Absence | 0.00 | -0.01 | pH < 6.8 |
| 5 | | 3.0 | 0.2 | 0.2 | 0.22 | 0.15 | 0.07 | Absence | 0.00 | 0.00 | pH < 6.8 |
| 6 | | 4.0 | 0.2 | 0.2 | 0.30 | 0.19 | 0.10 | Absence | 0.00 | 0.00 | pH < 6.8 |
| 7 | | 5.0 | 0.2 | 0.2 | 0.35 | 0.24 | 0.12 | Absence | 0.00 | 0.01 | pH < 6.8 |
| 8 | Case with coloring agent | 0.0 | 0.2 | 0.2 | 0.00 | 0.06 | 0.17 | Presence | 0.17 | 0.06 | pH < 6.8 |
| 9 | | 1.0 | 0.2 | 0.2 | 0.08 | 0.10 | 0.20 | Presence | 0.17 | 0.05 | pH < 6.8 |
| 10 | | 2.0 | 0.2 | 0.2 | 0.15 | 0.15 | 0.23 | Presence | 0.17 | 0.05 | pH < 6.8 |
| 11 | | 3.0 | 0.2 | 0.2 | 0.22 | 0.21 | 0.25 | Presence | 0.17 | 0.06 | pH < 6.8 |
| 12 | | 4.0 | 0.2 | 0.2 | 0.30 | 0.25 | 0.27 | Presence | 0.17 | 0.05 | pH < 6.8 |
| 13 | | 5.0 | 0.2 | 0.2 | 0.36 | 0.30 | 0.29 | Presence | 0.17 | 0.06 | pH < 6.8 |
| 14 | Case without adding second reagent | 0.0 | 0.2 | 0 | 0.00 | 0.01 | 0.10 | Presence | 0.10 | 0.01 | pH < 6.8 |
| 15 | | 1.0 | 0.2 | 0 | 0.00 | 0.01 | 0.10 | Presence | 0.10 | 0.01 | pH < 6.8 |
| 16 | | 2.0 | 0.2 | 0 | 0.00 | 0.01 | 0.10 | Presence | 0.10 | 0.01 | pH < 6.8 |
| 17 | | 3.0 | 0.2 | 0 | 0.00 | 0.01 | 0.10 | Presence | 0.10 | 0.01 | pH < 6.8 |
| 18 | | 4.0 | 0.2 | 0 | 0.00 | 0.01 | 0.10 | Presence | 0.10 | 0.01 | pH < 6.8 |
| 19 | | 5.0 | 0.2 | 0 | 0.00 | 0.01 | 0.10 | Presence | 0.10 | 0.01 | pH < 6.8 |
| 20 | Case without adding first reagent | 0.0 | 0 | 0.2 | 0.00 | 0.00 | 0.08 | Presence | 0.08 | 0.00 | pH < 6.8 |
| 21 | | 1.0 | 0 | 0.2 | 0.00 | 0.00 | 0.08 | Presence | 0.08 | 0.00 | pH < 6.8 |
| 22 | | 2.0 | 0 | 0.2 | 0.00 | 0.00 | 0.08 | Presence | 0.08 | 0.00 | pH < 6.8 |
| 23 | | 3.0 | 0 | 0.2 | 0.00 | 0.00 | 0.08 | Presence | 0.08 | 0.00 | pH < 6.8 |
| 24 | | 4.0 | 0 | 0.2 | 0.00 | 0.01 | 0.09 | Presence | 0.09 | 0.01 | pH < 6.8 |
| 25 | | 5.0 | 0 | 0.2 | 0.00 | 0.01 | 0.09 | Presence | 0.09 | 0.01 | pH < 6.8 |

FIG. 10

| Data No | Case | Phosphate ion concentration (mg/L) | Reagent addition concentration (mg/10mL) | | Value of absorbances | | | Presence or absence of coloring agent | Criterion formula (3) related to value of Ba - 0.34Ra | Criterion formula (4) related to value of Ga - 0.66Ra | pH of measuring water and the like |
|---|---|---|---|---|---|---|---|---|---|---|---|
| | | | First reagent | Second reagent | R Region component light $R\ a$ | G Region component light $G\ a$ | B Region component light $B\ a$ | | | | |
| 26 | Alkaline case without adding second reagent | 0.0 | 0.2 | 0 | 0.01 | 0.45 | 0.03 | Presence | 0.03 | 0.44 | pH > 8.4 |
| 27 | | 1.0 | 0.2 | 0 | 0.02 | 0.44 | 0.04 | Presence | 0.03 | 0.43 | pH > 8.4 |
| 28 | | 2.0 | 0.2 | 0 | 0.02 | 0.44 | 0.03 | Presence | 0.02 | 0.43 | pH > 8.4 |
| 29 | | 3.0 | 0.2 | 0 | 0.01 | 0.45 | 0.04 | Presence | 0.04 | 0.44 | pH > 8.4 |
| 30 | | 4.0 | 0.2 | 0 | 0.02 | 0.44 | 0.04 | Presence | 0.03 | 0.43 | pH > 8.4 |
| 31 | | 5.0 | 0.2 | 0 | 0.02 | 0.44 | 0.04 | Presence | 0.03 | 0.43 | pH > 8.4 |
| 32 | Alkaline case with coloring agent | 0.0 | 0.2 | 0.2 | 0.02 | 0.44 | 0.11 | Presence | 0.11 | 0.43 | pH > 8.4 |
| 33 | | 1.0 | 0.2 | 0.2 | 0.09 | 0.48 | 0.14 | Presence | 0.11 | 0.42 | pH > 8.4 |
| 34 | | 2.0 | 0.2 | 0.2 | 0.17 | 0.54 | 0.17 | Presence | 0.11 | 0.42 | pH > 8.4 |
| 35 | | 3.0 | 0.2 | 0.2 | 0.24 | 0.59 | 0.19 | Presence | 0.11 | 0.43 | pH > 8.4 |
| 36 | | 4.0 | 0.2 | 0.2 | 0.32 | 0.64 | 0.21 | Presence | 0.11 | 0.43 | pH > 8.4 |
| 37 | | 5.0 | 0.2 | 0.2 | 0.38 | 0.68 | 0.23 | Presence | 0.11 | 0.44 | pH > 8.4 |

METHOD FOR AUTOMATICALLY MEASURING CONCENTRATION OF DISSOLVED SUBSTANCE

CROSS-REFERENCE TO RELATED APPLICATION

This is a Continuation application of Ser. No. 14/440,523 filed on May 4, 2015, which is a PCT National Phase of PCT/JP2013/078184 filed on Oct. 17, 2013, claiming priorities of Japanese Patent Applications No. 2012-244753 filed on Nov. 6, 2012 and No. 2013-207840 filed on Oct. 3, 2013, the disclosure of which is incorporated herein.

FIELD OF TECHNOLOGY

The present invention relates to a method for automatically measuring concentration of a dissolved substance, which can also judge the presence or absence of addition of a reagent in a case wherein the concentration of the dissolved substance is measured using absorbance of a transmitted light which results from a light to penetrate a measuring water made by adding the reagent to a sample water.

BACKGROUND ART

It is necessary to monitor the quality of water used in facilities using an online monitoring apparatus in order to stably and effectively operate a water utilizing facility. In such a monitoring apparatus, for example, the concentration of a specific dissolved substance in the sample water is automatically measured by absorptiometry. In that case, in the absorptiometry, it is necessary to make measuring waters in which colors are developed by respectively adding, for example, a plurality of kinds of reagents to sample waters, and transmit lights to the measuring waters.

However, in such a monitoring apparatus, it may cause a case wherein a part of reagents is not added to the sample water because of a bad condition of a reagent pump or the depleting of the reagent. This may cause not only a wrong judgement of the quality of the sample water due to a lack of a correct measuring result, but also a problem of damaging the apparatus under the effect of other reagents.

Meanwhile, as for a method for preventing non-addition of the reagent, for example, there can be considered a method for providing a device to detect a remaining quantity of the reagent to a reagent bottle (Patent Document 1); a method for estimating the remaining quantity of the reagent from an operating time of an apparatus sending out the reagent (for example, the reagent pump); or a method for judging the presence or absence of addition of the reagent on the basis of the presence or absence of an indicator by adding the indicator (for example, a coloring agent), which develops a color different from a color developed by the reagent, to the reagent (Patent Documents 2 and 3).

PRIOR ART DOCUMENT

Patent Document

Patent Document 1: Japanese Unexamined Patent Application Publication No. H05-10958
Patent Document 2: Japanese Unexamined Patent Application Publication No. 2006-46985
Patent Document 3: Japanese Unexamined Patent Application Publication No. 2006-346613

SUMMARY OF THE INVENTION

Problems to be Solved by the Invention

The method for providing the device to detect the remaining quantity of the reagent, however, requires high cost since an additional device is necessary. Also, in this method, since there is a concern of a breakdown and the like due to complexity of equipment, a highly reliable detection regarding the non-addition of the reagent cannot be carried out.

Also, in the method for estimating the remaining quantity of the reagent from the operating time of the reagent pump, in a case wherein abnormality occurs in the reagent pump, the non-addition of the reagent cannot be judged.

Also, the method for adding the indicator to the reagent is an effective method in a case of using only one reagent; however, a plurality of reagents is separately added, so that a plurality of colors is developed by the indicators other than the colors developed by the reagents so as to be difficult to detect the colors developed by the reagents and be impractical. Also, this method requires a plurality of sets of light emitting devices and light receiving devices to detect the color developed in the measuring water, so that the cost of this method becomes high. Furthermore, this method has the concerns for a breakdown and the like due to complexity of the apparatus, so that the highly reliable detection regarding the non-addition of the reagent cannot be carried out.

In view of the above-mentioned problems, an object of the present invention is to provide a method for automatically measuring concentration of a dissolved substance which can judge the presence or absence of addition of the reagent reliably at low cost in a case wherein the concentration of the specific dissolved substance is measured by the absorptiometry using the measuring water wherein the plurality of reagents is separately added to the sample water.

Means for Solving the Problems

A method for automatically measuring concentration of a dissolved substance according to the first aspect of the present invention comprises a step of making a measuring water, of which a pH value is kept within a specific pH range, and which develops a specific color by a specific dissolved substance in a sample water, by adding respectively two kinds of reagents to the sample water sampled from a target water system; a step of selecting one acid-base indicator which can develop respectively different colors other than the specific color in a first pH range including the specific pH range, and a second pH range deviating from the first pH range; a step of preparing reagents in which in a case wherein one of pH values of reagent added waters, in which each one kind of the two kinds of reagents is added to the sample water, is within the second pH range, the selected acid-base indicator is added to one reagent added to the reagent added water on a side within the second pH range to prepare a reagent, and in a case wherein neither of the pH values of the reagent added waters is within the second pH range, the selected acid-base indicator and a pH regulator for making the pH value of the reagent added water within the second pH range are added to one reagent added to the reagent added water wherein the pH value is on a side close to the second pH range, and another pH regulator for neutralizing the pH regulator added to the one reagent is added to the other reagent; a step of calculating each of absorbances with respect to a red region component light, a green region component light, and a blue region component light obtained by dividing a light in a visible light region of a transmitted light of the measuring water into nearly three parts by emitting a light to the measuring water made by respectively adding the two kinds of prepared reagents to the sample water; a step of judging the presence or absence of addition of the two kinds of reagents relative to the sample water using the calculated absorbances; and a step of calculating concentration of the specific dissolved substance in the sample water using the calculated absorbances.

For example, in a case wherein the pH value of the reagent added water made by adding one reagent (hereinafter referred to as a first reagent) to the sample water is within the second pH range, a preparation of the reagent is carried out by adding the selected acid-base indicator (hereinafter referred to as a selected indicator) to the first reagent. In this case, nothing is added to the other reagent (hereinafter referred to as a second reagent). Also, in a case wherein neither of the pH values of the reagent added waters is within the second pH range, the preparation of the reagent is carried out by adding the selected indicator to one reagent (hereinafter referred to as the first reagent) added to the reagent added water, of which the pH value is close to the second pH range. In this case, the preparation of the reagents is carried out by adding the pH regulator to the first reagent so that the pH value of the reagent added water is within the second pH range, and by adding another pH regulator for neutralizing the pH regulator added to the first reagent, to the other reagent (hereinafter referred to as the second reagent). Then, the measuring water is made by adding the prepared first reagent and second reagent to the sample water.

When the prepared first reagent and second reagent are added together to the sample water, the measuring water develops the specific color by the specific dissolved substance in the sample water, and the pH value falls within the specific pH range, so that the measuring water develops one color (hereinafter referred to as the first color) of respectively different colors other than the specific color by the selected indicator in the first reagent. Also, in a case wherein only the first reagent is added to the sample water and the second reagent is not added, the pH value of the measuring water falls within the second pH range, and the measuring water develops the other color (hereinafter referred to as the second color) of respectively different colors other than the specific color by the selected indicator of the first reagent. Moreover, in a case wherein the first reagent is not added to the sample water, since the measuring water does not include the selected indicator, neither the first color nor the second color is developed. Namely, if the measuring water develops any of the first color or the second color, it is judged that the first reagent is added, and if the measuring water develops neither the first color nor the second color, it is judged that the first reagent is not added. Then, in a case wherein the first reagent is judged to be added, if the measuring water develops the first color, it can be judged that the second reagent is added to the measuring water as well, and if the measuring water develops the second color, it can be judged that the second reagent is not added to the measuring water.

On the other hand, the absorbances of the measuring water are calculated with respect to the red region component light, the green region component light, and the blue region component light obtained by dividing the light in the visible light region of the transmitted light of the measuring water into nearly three parts. Then, for example, whether or not the measuring water developing the specific color is developing the first color can be judged using a computing equation wherein any of the absorbances with respect to three region component lights is a function. Namely, a computing equation to eliminate the effect of a color development to the specific color is considered, and if a value of the computing equation obtained from values of the absorbances with respect to the three region component lights falls within a specific range by the effect of the first color, the measuring water is judged as developing the first color. Incidentally, whether or not the measuring water is developing the second color can be judged as well in the same manner based on the value of the computing equation wherein any of the absorbances with respect to the three region component lights is a function.

Also, the concentration of the specific dissolved substance in the sample water can be obtained from an absorbance value of the measuring water developing the specific color by obtaining beforehand a relation between the absorbance (for details, each absorbance with respect to the three region component lights) of the measuring water developing the specific color and the concentration of the specific dissolved substance. Here, the measuring water wherein the first reagent and the second reagent are added together is developing the specific color and the first color; however, the absorbance of the measuring water developing the first color becomes a fixed value regardless of a value of the concentration of the specific dissolved substance so as to be predicted beforehand. Therefore, the absorbance value of the measuring water developing the specific color can be obtained by subtracting the absorbance value of the measuring water developing the first color from the absorbance value of the measuring water developing the specific color and the first color.

The method for automatically measuring concentration of a dissolved substance according to a second aspect of the present invention comprises a step of making a measuring water, of which a pH value falls within a specific pH range, and which develops a specific color by a specific dissolved substance in a sample water, by adding respectively two kinds of reagents to the sample water sampled from a target water system; a step of selecting one acid-base indicator which can develop respectively different colors other than the specific color in a first pH range including the specific pH range, and a second pH range deviating from the first pH range; a step of preparing reagents by adding the selected acid-base indicator to one reagent of the two kinds of reagents, and by adding the selected acid-base indicator or a coloring agent developing the same color that the selected acid-base indicator develops in the specific pH range, to the other reagent of the two kinds of reagents; a step of calculating each of the absorbances with respect to a red region component light, a green region component light, and a blue region component light obtained by dividing a light in a visible light region of a transmitted light of the measuring water by emitting a light to the measuring water made by respectively adding the two kinds of prepared reagents to the sample water; a step of judging the presence or absence of addition of the two kinds of reagents relative to the sample water using the calculated absorbances, and of judging an unusual pH value of the sample water; and a step of calculating the concentration of the specific dissolved substance in the sample water using the calculated absorbances.

First, a case wherein the selected acid-base indicator (hereinafter referred to as the selected indicator) is added respectively to one reagent (hereinafter referred to as the first reagent) and the other reagent (hereinafter referred to as the second reagent), will be explained.

The measuring water, wherein the first reagent and the second reagent are added together to the sample water, develops the specific color by the specific dissolved substance in the sample water, and the pH value falls within the specific pH range, so that the measuring water deeply (strongly) develops one (hereinafter referred to as the first color) of respectively different colors other than the specific color by the selected indicator in the first reagent and the second reagent. Also, the measuring water, wherein only one of the first reagent or the second reagent is added to the sample water, develops the first color or the other (hereinafter referred to as the second color) and the like of respectively different colors other than the specific color based on the pH value thereof, and does not develop deeply (strongly) the first color. Moreover, the measuring water, wherein the first reagent and the second reagent are added together to the sample water having the unusual pH value, develops deeply (strongly) the second color by the selected indicator in the first reagent and the second reagent when the pH value thereof falls within the second pH range.

Namely, the measuring water wherein the first reagent and the second reagent are added together; the measuring water wherein only one of the first reagent or the second reagent is added; and the measuring water having the unusual pH value of the sample water even if the first reagent and the second reagent are added together, have respectively a difference in a color developed based on the selected indicator or depth (strength) of the developed color. Therefore, regarding each of the aforementioned differences, a computing equation, wherein any of the absorbances with respect to the three region component lights is a function, is considered, and if a type of the color or a contrasting density of the color developed in the measuring water is judged based on a value of the computing equation, it can be easily judged whether the first reagent and the second reagent are added together or not, or whether the pH value of the sample water is unusual or not.

Next, a case wherein the selected indicator is added to one reagent (hereinafter referred to as the first reagent), and the coloring agent is added to the other reagent (hereinafter referred to as the second reagent), will be explained.

Even in this case, the measuring water wherein the first reagent and the second reagent are added together to the sample water develops the specific color by the specific dissolved substance in the sample water, and develops deeply (strongly) one (hereinafter referred to as the first color) of respectively different colors other than the specific color by the selected indicator in the first reagent and the coloring agent in the second reagent. Also, the measuring water wherein only one of the first reagent or the second reagent is added to the sample water develops the first color or the other (hereinafter referred to as the second color) and the like of the respectively different colors other than the specific color based on the pH value thereof by the selected indicator in the first reagent, or develops the first color by the coloring agent in the second reagent. Namely, the measuring water wherein only one of the first reagent or the second reagent is added to the sample water may develop the first color; however, it never develops deeply (strongly) the first color. Therefore, a computing equation, wherein any of the absorbances with respect to the three region component lights is a function, is considered, and if whether or not the measuring water is developing the first color deeply (strongly) is judged based on a value of the computing equation, it can be easily judged whether the first reagent and the second reagent are added together or not.

Also, in a case wherein the pH value of the measuring water made by adding only the first reagent to the sample water is within the first pH range, the measuring water made by adding one of the first reagent or the second reagent, or both of the first reagent and the second reagent to the sample water does not develop the second color by the selected indicator. However, even in such a case, if the pH value of the measuring water falls within the second pH range since the pH value of the sample water is unusual, the measuring water develops the second color. Therefore, in such a case as well, a computing equation, wherein any of the absorbances with respect to the three region component lights is a function, is considered, and if whether or not the measuring water is developing the second color is judged based on a value of the computing equation, it can be easily judged whether the pH value of the sample water is unusual or not.

Effect of the Invention

According to the present invention of the first aspect, the presence or absence of the addition of one reagent of the two kinds of reagents, wherein the acid-base indicator is added, relative to the sample water can be reliably judged only by adding the selected acid-base indicator to one of the two kinds of reagents, or by adding the selected acid-base indicator and the pH regulator to one of the two kinds of reagents, and adding another pH regulator to the other of the two kinds of reagents. Then, if the one reagent is judged to be added, based on the difference of the color developed in the measuring water, the presence or absence of the addition of the other reagent can be judged as well. Therefore, in the present invention, the presence or absence of the addition of the reagent can be judged at relatively low cost. Also, in the present invention, a wavelength range of the visible light region of the transmitted light from the measuring water is divided into the three region component lights, and the absorbances with respect to the three region component lights can be calculated simultaneously, so that even if the measuring water develops any color tone, it is sufficient that the light emitting device and the light receiving device are provided as a set. Therefore, in the present invention, a highly reliable judgment regarding the presence or absence of the addition of the reagent can be carried out without complicating an apparatus.

According to the present invention of the second aspect, the presence or absence of the addition of the two kinds of reagents relative to the sample water can be reliably judged by adding the selected acid-base indicator to one of the two kinds of reagents, and only adding the selected acid-base indicator or the coloring agent to the other of the two kinds of reagents. Therefore, in the present invention, the presence or absence of the addition of the reagents can be judged at relatively low cost. Also, in the present invention, the light emitting device and the light receiving device are only required to be a set so as not to complicate the apparatus, and the highly reliable judgment regarding the presence or absence of the addition of the reagents can be carried out. Furthermore, in the present invention, even in a case wherein the pH value of the sample water is unusual, the unusual pH value of the sample water can be judged reliably under certain conditions. Accordingly, the occurrence of an error of the measurement of the concentration of the dissolved substance due to the unusual pH value of the sample water can be prevented.

BRIEF DESCRIPTION OF THE DRAWINGS

FIG. 5 is a table showing experimental data for investigating conditions of addition of reagents with respect to a concentration measurement of free residual chlorine.

FIG. 7 is a table showing in detail a step of judging the presence or absence of addition of the reagents shown in FIG. 6.

FIG. 8 is a table showing other details of the step of judging the presence or absence of the addition of the reagents shown in FIG. 6.

FIG. 9 is a table showing experimental data for investigating the conditions of the addition of the reagents and the like with respect to a concentration measurement of phosphate ion.

FIG. 10 is a table showing experimental data continued from the experimental data in FIG. 9.

BEST MODES OF CARRYING OUT THE INVENTION

Hereinafter, embodiments of the present invention will be explained with reference to the drawings.

First Embodiment

First, with reference to FIG. 1, a concentration measuring apparatus for carrying out the present invention will be explained.

A concentration measuring apparatus 1 automatically measures concentration of a specific dissolved substance in a sample water W0 sampled from a target water system, for example, such as an industrial water system or a domestic water system by absorptiometry. In the concentration measuring apparatus 1, the concentration of the specific dissolved substance is measured using an absorbance of a light obtained by transmitting a light to a measuring water developed a color by adding two kinds of reagents respectively to the sample water W0. Incidentally, in order to measure the concentration of the specific dissolved substance, it is necessary to add the two kinds of reagents separately to the sample water W0.

Figure 1:
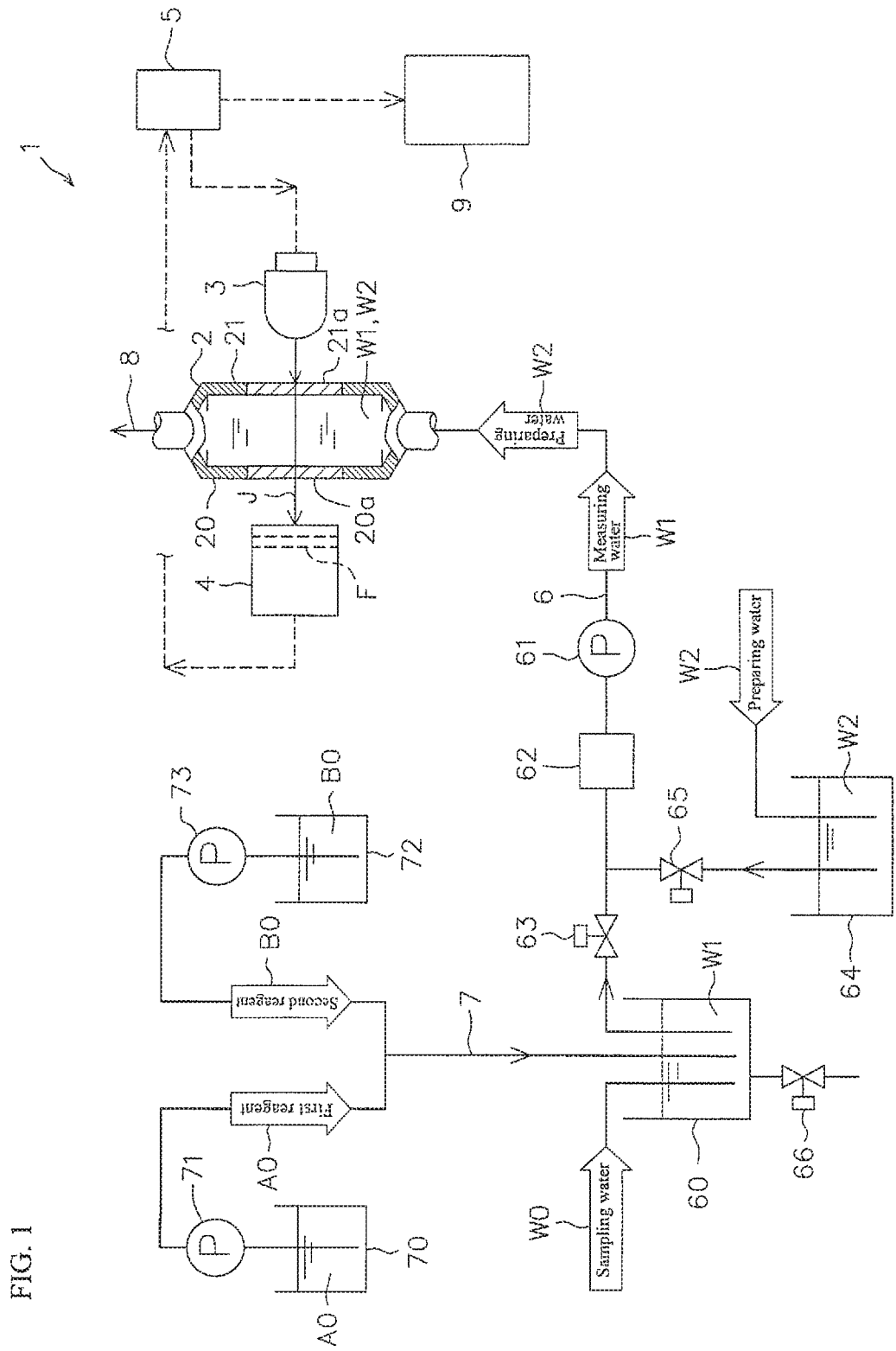
FIG. 1 is a drawing showing a concentration measuring apparatus for carrying out the present invention.

As shown in FIG. 1, the concentration measuring apparatus 1 includes a measuring cell 2 wherein a colored measuring water W1 or a clear preparing water W2 passes therethrough; a light emitting device 3 provided on one lateral face side of the measuring cell 2, and developing a measuring light inside the measuring cell 2; a light receiving device 4 provided on the other lateral face side of the measuring cell 2, and receiving the light from the light emitting device 3 penetrated through the measuring cell 2; an input/output portion 5 relative to the light emitting device 3 and the light receiving device 4; a supply line 6 supplying the measuring water W1 or the preparing water W2 to the measuring cell 2; a reagent supply line 7 supplying the two kinds of reagents, i.e., a first reagent A0 and a second reagent B0 to the supply line 6; a discharge line 8 discharging the measuring water W1 or the preparing water W2 from the measuring cell 2; and a computing processing apparatus 9 wherein an output signal (a transmitted light strength signal) from the input/output portion 5 is entered.

Here, as shown in FIG. 1, the supply line 6 includes a tube pump 61, a strainer 62, and an electromagnetic valve 63 in a pipe between a measuring water container 60 where the measuring water W1 is stored and the measuring cell 2. Also, in the supply line 6, a preparing water container 64 where the preparing water W2 is stored and a downstream-side pipe of the electromagnetic valve 63 are connected by a pipe wherein an electromagnetic valve 65 is provided. The reagent supply line includes a pump 71 in a pipe connecting between a first reagent container 70 where the first reagent A0 is stored, and the measuring water container 60. Also, the reagent supply line 7 includes a pump 73 in a pipe connecting between a second reagent container 72 where the second reagent B0 is stored, and the measuring water container 60. Incidentally, the sample water W0 can be supplied to the measuring water container 60, and the preparing water W2 can be supplied to the preparing water container 64. Also, an electromagnetic valve 66 discharging the measuring water W1 is provided inside a drainage pipe of the measuring water container 60.

As shown in FIG. 1, the supply line 6 is connected to a lower part of the measuring cell 2, and the discharge line 8 is connected to an upper part of the measuring cell 2, and the measuring water W1 or the preparing water W2 is passed through an inner flow channel. In the measuring cell 2, there are formed transparent portions 20a and 21a at positions facing each other in right and left lateral face portions 20 and 21. For example, the light emitting device 3 is disposed on a transparent portion 21a side, and the light receiving device 4 is disposed on a transparent portion 20a side by matching an optical axis so as to face the light emitting device 3.

The light emitting device 3 emits a light into the measuring cell 2, and transmits the light into the measuring water W1 or the preparing water W2 inside the measuring cell 2. In the light emitting device 3, there is used a light source such as, for example, a light-emitting diode (LED) emitting a light (a white light) including a visible light region.

The light receiving device 4 receives a transmitted light J transmitted through the measuring water W1 or the preparing water W2 inside the measuring cell 2 among lights emitted from the light emitting device 3, and measures the strength of the transmitted light J. The light receiving device 4 includes three photodiodes, and three color filters F, i.e., an R filter, a G filter, and a B filter respectively transmitting only a red region component light (hereinafter referred to as an R region component light), a green region component light (hereinafter referred to as a G region component light), or a blue region component light (hereinafter referred to as a B region component light) obtained by dividing a wavelength range of a light in the visible light region into roughly three.

Figure 2:
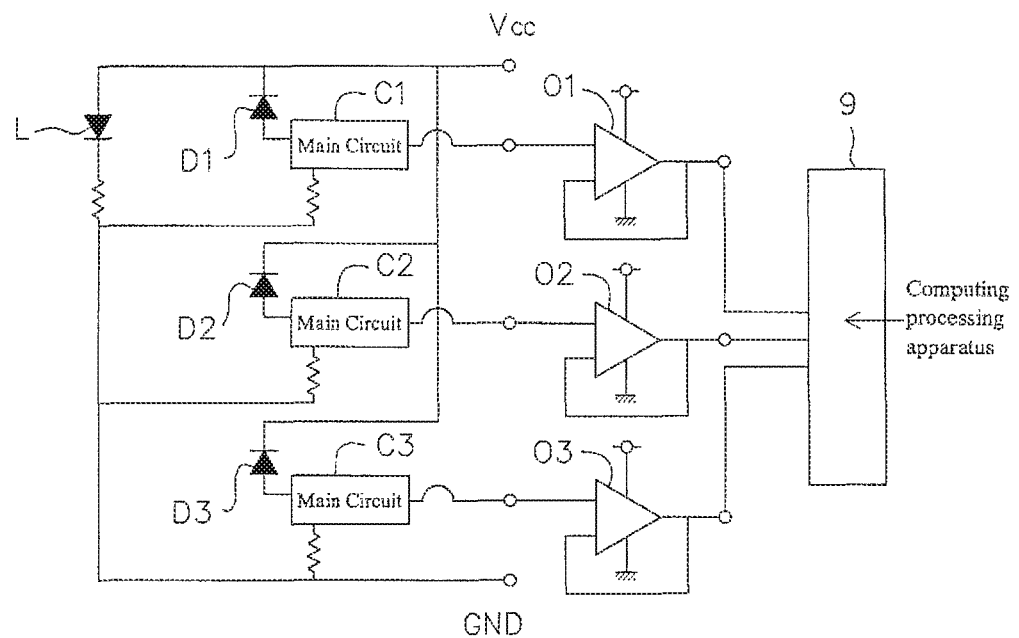
FIG. 2 is an electric wiring diagram inside an input/output portion wherein a light emitting device and a light receiving device are added.

Namely, in the light receiving device 4, there is used an RGB color sensor including a photodiode D1 having the R filter, a photodiode D2 having the G filter, and a photodiode D3 having the B filter (see FIG. 2). Then, the light receiving device 4 simultaneously measures the strengths of the respective lights of the R region component light, the G region component light, and the B region component light (hereinafter referred to as three region component lights) transmitted through each filter within the transmitted light J transmitted through the measuring water W1 and the like. Incidentally, the R filter transmits a red light the most within the R region component light, and the G filter transmits a green light the most within the G region component light, and the B filter transmits a blue light the most within the B region component light.

The input/output portion 5 includes a control circuit for the light emitting device 3 and for the light receiving device 4. FIG. 2 shows an electric wiring diagram inside the input/output portion 5 wherein the light emitting device 3 and the light receiving device 4 are added. In the drawing, the reference symbol D1 represents the photodiode having the R filter; the reference symbol D2 represents the photodiode having the G filter; and the reference symbol D3 represents the photodiode having the B filter. Then, the aforementioned photodiodes are integrated to form the light receiving device 4. Also, in the drawing, the reference symbol L represents the light-emitting diode (LED) which becomes the light emitting device 3; the reference symbols C1, C2, and C3 represent main circuits for the respective photodiodes D1, D2, and D3; and the reference symbols O1, O2, and O3 represent Op-Amps (operational amplifiers) for the respective photodiodes D1, D2, and D3. A signal of a transmitted light strength of each region component light output from the light receiving device 4 is transmitted to the computing processing apparatus 9 through the Op-Amps O1, O2, and O3.

The computing processing apparatus 9 includes a computing portion, a memory portion, and a display portion. The computing portion calculates a time average strength with respect to each region component light based on, for example, the signal of the light strength with respect to the three region component lights output from the light receiving device 4. Also, the computing portion calculates absorbances with respect to the three region component lights using, for example, the transmitted light strength wherein one portion of the light is absorbed, and the transmitted light strength wherein the light is not absorbed, and calculates concentration of a dissolved substance which is measured from a value of each of the absorbances with respect to the three region component lights. The memory portion stores, for example, a table showing a relation between the value of each absorbance and the concentration of the dissolved substance with respect to the three region component lights by each kind of the dissolved substance and the like. The display portion displays, for example, the concentration of the dissolved substance calculated in the computing portion and the like. Incidentally, the computing processing apparatus 9 additionally has the later-described other functions.

In order to measure the concentration of the specific dissolved substance inside the sample water W0 using the concentration measuring apparatus 1, first, a specific quantity of the sample water W0 is introduced into the measuring water container 60. Next, the first reagent A0 inside the first reagent container 70 and the second reagent B0 inside the second reagent container 72 are added to the sample water W0 by each necessary quantity using the pumps 71 and 73. Next, the sample water W0 to which the first reagent A0 and the second reagent B0 are added together is sufficiently stirred, and then, when the aforementioned sample water W0 is left at a certain temperature (for example, 20 to 40 degrees C.) for a certain time (for example, 15 minutes), the measuring water W1 developing a specific color by the specific dissolved substance is made. In that case, the depth of the color of the measuring water W1 varies by the concentration of the dissolved substance.

Next, the clear preparing water W2 which does not absorb the light, for example, a pure water is passed to the measuring cell 2 with, for example, a flow rate of 10 mL per a minute, for example, for three minutes by switching the electromagnetic valves 63 and 65 and using a tube pump 61. When the passing water into the measuring cell 2 halts, a light is emitted into the preparing water W2 through the transparent portions 20a and 21a of the measuring cell 2 from the light emitting device 3, for example, for one minute. Thereby, the light including the visible light region from the light emitting device 3 transmits the preparing water W2, and is received by the light receiving device 4. In that case, the light receiving device 4 receives the transmitted light J of the preparing water W2 from the light emitting device 3 through the three color filters F, so that the light receiving device 4 simultaneously measures each of the strengths of the three region component lights wherein the wavelength range of the light in the visible light region is divided into roughly three. Then, the computing processing apparatus 9 calculates an average strength of the respective three region component lights in a case wherein the light is not absorbed (transmittance 100%) by averaging output values from the light receiving device 4 during one minute.

Next, the measuring water W1 developing the specific color by the specific dissolved substance is passed to the measuring cell 2 with the flow rate of 10 mL per a minute for three minutes as with the case of the preparing water W2. After the aforementioned water passing halts, a light from the light emitting device 3 is penetrated into the measuring water W1 for one minute, and the light receiving device 4 receives the transmitted light J. The light receiving device 4 measures each of the strengths of the three region component lights wherein one portion of the light is absorbed by the measuring water W1. The computing processing apparatus 9 calculates an average strength of the respective three region component lights wherein the light of one portion is absorbed by the measuring water W1 by averaging output values from the light receiving device 4 during one minute, and calculates an average strength of the three region component lights measured using the preparing water W2 having the transmittance 100%. Next, the computing processing apparatus 9 calculates each of the absorbances with respect to the three region component lights using the aforementioned average strength. Next, the computing processing apparatus 9 calculates the concentration of the specific dissolved substance in the sample water W0 using the calculated absorbance value from the relation between each absorbance with respect to the three region component lights and the concentration of the specific dissolved substance, stored with respect to the specific dissolved substance, and displays a value thereof.

However, when the concentration of the specific dissolved substance is automatically measured by the aforementioned concentration measuring apparatus 1, in a case wherein the concentration of the specific dissolved substance in the sample water W0 shows a result of zero, there is a question whether the first reagent A0 and the second reagent B0 are surely added to the sample water W0 or not. This is because such reagents are not added due to run-out of the reagents inside the first reagent container 70 or the second reagent container 72, or a breakdown of the pumps 71 and 73 and the like. Therefore, when the concentration of the dissolved substance is automatically measured, it is important that the presence or absence of addition of the reagents can be judged.

Next, a method for automatically measuring concentration of a dissolved substance according to one embodiment of the present invention will be explained with reference to FIG. 4. In this method, especially, the presence or absence of the addition of the reagents is judged.

Figure 4:
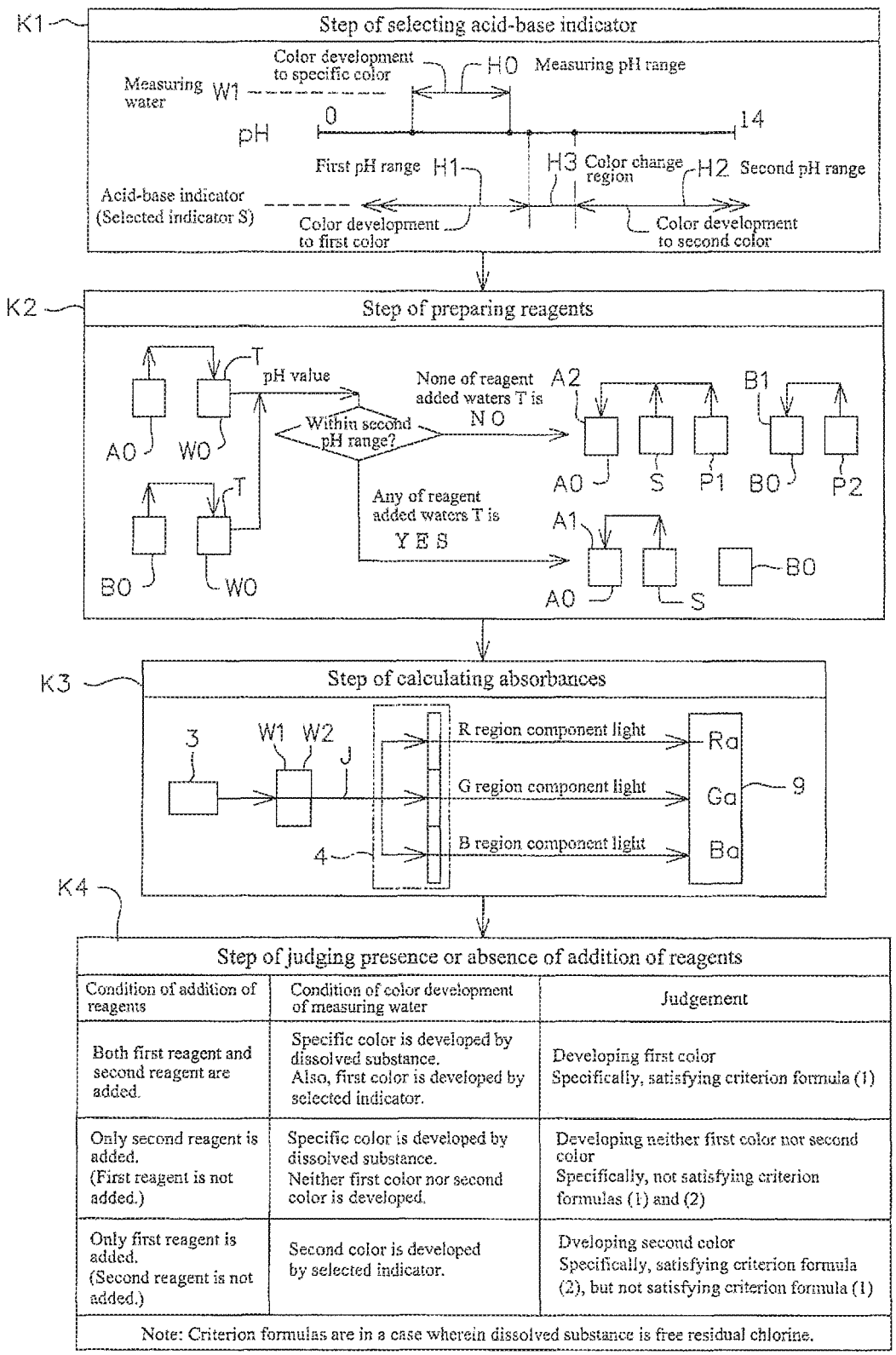
FIG. 4 is a flowchart showing a method for automatically measuring concentration of a dissolved substance according to one embodiment of the present invention.

The method for automatically measuring concentration of a dissolved substance includes a step of making the measuring water, a step of calculating the concentration of the dissolved substance, and the like, and as characteristic steps, as shown in FIG. 4, the method for automatically measuring concentration of a dissolved substance includes a step K1 of selecting an acid-base indicator; a step K2 of preparing the reagents; a step K3 of calculating the absorbances; and a step K4 of judging the presence or absence of the addition of the reagents.

In the step K1 of selecting the acid-base indicator, an acid-base indicator suitable for a concentration measurement of the specific dissolved substance is selected from a plurality of acid-base indicators. In a case wherein the concentration of the specific dissolved substance is measured by adding a prescribed reagent by each dissolved substance to the sample water W0, the measuring water W1 develops a specific color in a state of being held in a specific pH range (hereinafter referred to as a measuring pH range H0). Also, there are many acid-base indicators which, for example, develop a first color within a first pH range H1, and develop a second color different from the first color within a second pH range H2 beyond a color change region H3. Then, an acid-base indicator to be selected (hereinafter referred to as a selected indicator S) is the acid-base indicator, for example, developing the first color within the first pH range H1 including the measuring pH range H0, and developing the second color different from the first color within another pH range (hereinafter referred to as a second pH range H2) deviating from the first pH range H1, and it is sufficient that the first color and the second color are different from the specific color by the dissolved substance.

The acid-base indicator is an indicator changing a color tone by a pH value. The acid-base indicator includes, for example, methyl violet, thymol blue, methyl yellow, bromophenol blue, methyl orange, litmus, bromothymol blue, phenol red, phenolphthalein, thymolphthalein, alizarin yellow, o-cresol red, and the like. Incidentally, in the acid-base indicator, in order to increase solubility, there is added a solubility improver such as alcohols, glycols, diol, and triols; however, hereinafter the aforementioned solubility improver is also included as the acid-base indicator.

The step K2 of preparing the reagents is carried out for developing a color different from the specific color by the dissolved substance in the measuring water W1. In the step K2 of preparing the reagents, the selected indicator S or a pH regulator P1 or P2 is added to the first reagent A0 and the second reagent B0 as needed to prepare the reagents. Incidentally, hereinbefore, the measuring water W1 has been explained such that the first reagent A0 and the second reagent B0 are added together to the sample water W0; however, hereinafter, except for the preparing water W2, all waters which become a target for the concentration measurement are referred to as the measuring water W1.

In the step K2 of preparing the reagents, in a case wherein pH values of two reagent added waters T to which the first reagent A0 and the second reagent B0 are separately added to each of the sample waters W0 are within the second pH range H2, the selected indicator S is added to one of the reagents (for example, the first reagent A0) added to the reagent added water T on a side within the second pH range H2, and nothing is added to the other reagent (the second reagent B0). Also, in the step K2 of preparing the reagents, in a case wherein neither of the pH values of the reagent added waters T is within the second pH range H2, the selected indicator S is added to one reagent (for example, the first reagent A0) added to the reagent added water T on a side close to the second pH range H2, and in order to make the pH value of the reagent added water T within the pH range H2, the pH regulator P1 is added to the first reagent A0, and the other pH regulator P2 neutralizing the pH regulator P1 added to the first reagent A0 is added to the second reagent B0.

Namely, for example, in a case wherein the pH value of the reagent added water T, in which the first reagent A0 is added to the sample water W0 just in a necessary quantity for the concentration measurement, is within the second pH range H2, the selected indicator S is added to the first reagent A0 in a necessary quantity to make the first reagent A1, and nothing is added to the second reagent B0. Also, in the case wherein neither of the pH values of the reagent added waters T is within the second pH range H2, the pH regulator P1 is added just in a necessary quantity to the first reagent A0 together with the selected indicator S to make a first reagent A2 so that the pH value of the reagent added water T on the side close to the second pH range H2 (for example, the reagent added water T to which the first reagent A0 is added) falls within the second pH range H2, and the pH regulator P2 is added only for a quantity for neutralizing the pH regulator P1 to the second reagent B0 to make a second reagent B1.

In the step K3 of calculating the absorbances, each absorbance with respect to the three region component lights is calculated using the measuring water W1 wherein prepared first reagents A1 and A2, and second reagents B0 and B1 are added together to the sample water W0. The step K3 of calculating the absorbances has been described in detail in the explanation of the concentration measuring apparatus 1, so that a detailed explanation will be omitted here.

The step K4 of judging the presence or absence of the addition of the reagents judges whether the first reagents A1 and A2, and the second reagents B0 and B1 are added together, or only the first reagents A1 and A2 are added, or only the second reagents B0 and B1 are added, by the difference of color that the measuring water W1 develops. In a case wherein the first reagents A1 and A2, and the second reagents B0 and B1 are added together to the sample water W0, the measuring water W1 develops the specific color by the dissolved substance, and the first color by the selected indicator S of the first reagents A1 and A2. Also, in a case wherein only the second reagents B0 and B1 are added to the sample water W0, the selected indicator S is not included in the measuring water W1, so that the measuring water W1 does not develop any of the first color or the second color. Furthermore, in a case wherein only the first reagents A1 and A2 are added to the sample water W0, the pH value of the measuring water W1 falls within the second pH range, so that the measuring water W1 develops the second color by the selected indicator S of the first reagents A1 and A2. Therefore, if the measuring water W1 develops the first color, the first reagents A1 and A2, and the second reagents B0 and B1 are added together, and if the measuring water W1 develops the second color, only the first reagents A1 and A2 are added, and if the measuring water W1 develops none of the first color and the second color, only the second reagents B0 and B1 are added, or none of the reagents are added.

On the other hand, contrasting densities of color tones (the first color, the second color, and the specific color) developed by the measuring water W1 are shown with absorbance values Ra, Ga, and Ba with respect to the three region component lights. Then, for example, whether or not the measuring water W1 developing the specific color is developing the first color can be judged by considering a computing equation, wherein any of the absorbances with respect to the three region component lights is a function, and by judging whether a value of the computing equation using the absorbance values Ra, Ga, and Ba with respect to the three region component lights falls within a specific range or not. Also, whether or not the measuring water W1 is developing the second color can also be judged using the computing equation wherein any of the absorbances of the three region component lights is a function. Incidentally, a specific example of the computing equation will be explained in the later-described experimental example.

However, the respective absorbance values Ra, Ga, and Ba of the measuring water W1 developing the specific color, which are necessary for calculating the concentration of the specific dissolved substance, can be obtained by subtracting the respective absorbance values Ra, Ga, and Ba with respect to the first color from the respective absorbance values Ra, Ga, and Ba of the measuring water W1 developing the specific color and the first color. In that case, the absorbance values Ra, Ga, and Ba with respect to the first color are determined by the concentration of the first reagents A1 and A2 in the measuring water W1 without any relation to the concentration of the specific dissolved substance, and have fixed values so as to be predicted in advance.

As mentioned above, in the method for automatically measuring concentration of a dissolved substance, the presence or absence of the addition of the first reagents A1 and A2, and the second reagents B0 and B1 relative to the sample water W0 can be judged reliably by adding the selected indicator S to one of the first reagent A0 or the second reagent B0, or by adding the selected indicator S and the pH regulator P1 to one of the first reagent A0 or the second reagent B0, and only adding the other pH regulator P2 to the other of the first reagent A0 or the second reagent B0. Therefore, the method for automatically measuring concentration of a dissolved substance does not require large cost in order to judge the presence or absence of the addition of the reagents as well. Also, in the method for automatically measuring concentration of a dissolved substance, the transmitted light J from the measuring water W1 is divided into the three region component lights, and the absorbances with respect to the three region component lights can be simultaneously calculated, so that even if the measuring water W1 develops any color tone, it is sufficient that the light emitting device and the light receiving device are a set. Therefore, in the method for automatically measuring concentration of a dissolved substance, a highly reliable judgment regarding the presence or absence of the addition of the reagents can be carried out without complicating the apparatus.

Incidentally, the computing processing apparatus 9 additionally has a function of judging the presence or absence of the addition of the first reagents A1 and A2, and the second reagents B0 and B1, so that a judgement of the presence or absence of the addition of the reagents is automatically carried out by the concentration measuring apparatus 1.

Figure 3:
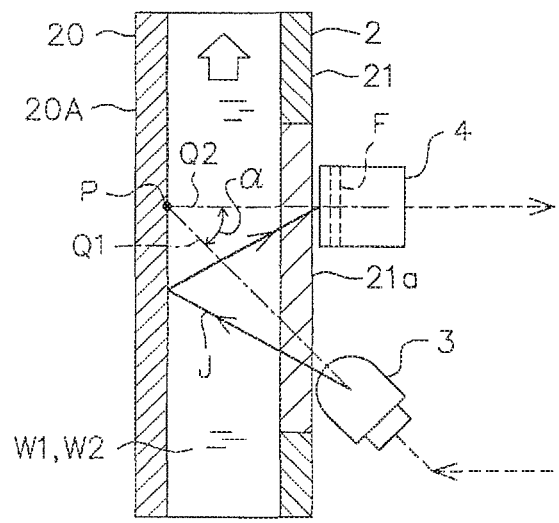
FIG. 3 is a drawing wherein the light emitting device and the light receiving device are disposed around a measuring cell having a different form.

Also, as shown in FIG. 3, the left lateral face portion 20 of the measuring cell 2 may be a reflection plate 20A, and the light emitting device 3 and the light receiving device 4 may be disposed on a right lateral face portion 21 side of the measuring cell 2. In the concentration measuring apparatus 1 having such a measuring cell 2 and the like, a light emitted from the light emitting device 3 can be passed through the measuring water W1 inside the measuring cell 2 twice by reflecting the light by the reflection plate 20A, so that a length of the transmitted light J in the measuring cell 2 increases, and to that extent, a distance between the right and left lateral face portions 20 and 21 of the measuring cell 2 can be reduced. Therefore, in such a concentration measuring apparatus 1, the measuring cell 2 can be downsized, and a quantity of the measuring water W1 supplied to the measuring cell 2 and the like can be reduced. Incidentally, the light emitting device 3 is tilted so that an optical axis Q1 thereof passes an intersection point P between an optical axis Q2 of the light receiving device 4 orthogonal to the reflection plate 20A and the reflection plate 20A, and is positioned so that an angle $\alpha$ between the optical axes Q1 and Q2 has approximately 45 degrees in a positional relationship to the light receiving device 4.

FIG. 5 shows data of the experimental example for investigating the presence or absence of the addition of the reagents. This experimental example relates to the concentration measurement of free residual chlorine, and as for the first reagent A0 (an alleviator), there is used a mixture solution of maleic acid and lithium hydroxide-hydrate, and as for the second reagent B0, there is used a mixture solution of DPD sulfate and sulfuric acid. The measuring water W1, wherein the first reagent A0 and the second reagent B0 are added together to the sample water W0 including the free residual chlorine, is maintained in a pH value of 4 to 7.8 and within the measuring pH range H0, and develops a red color (the specific color) by the free residual chlorine. As for the selected indicator S, there is used an indicator wherein diethylene glycol which becomes the solubility improver is added to thymol blue (which develops the red color with pH 1.2 or less, develops a yellow color with pH 2.8 to 7.8, and develops a blue color with pH 9.5 or above, respectively). In that case, a range of pH 2.8 to 7.8 where the thymol blue develops the yellow color (the first color) becomes the first pH range H1, and a range of pH 9.5 or above where the thymol blue develops the blue color (the second color) becomes the second pH range H2.

Here, a pH value of the reagent added water T wherein the first reagent A0 having a pH value on an alkali side is added to the sample water W0 is smaller than a value within the second pH range H2, so that the first reagent A2 is made by adding the selected indicator S and the pH regulator P1 on the alkali side to the first reagent A0. In that case, as for the pH regulator P1, a slightly larger quantity of the lithium hydroxide-hydrate is added to the first reagent A0; however, for the pH regulator P1, other alkaline chemicals may be used. Also, the second reagent B1 is made by adding the pH regulator P2 on an acid side neutralizing the pH regulator P1 to the second reagent B0. In that case, as for the pH regulator P2, a slightly larger quantity of the sulfuric acid is added to the second reagent B0; however, for the pH regulator P2, other acidic chemicals may be used.

The sample water W0 is made by adding sodium hypochlorite to a pure water, and is prepared so that the concentration of the free residual chlorine becomes 0.0 to 2.0 mg/L. The measuring water W1 is made by adding each 0.2 mL of the first reagent A2 and the second reagent B1 to 10 mL of the sample water W0. Incidentally, the pH value of the sample water W0 shows a value near 7.

In FIG. 5, a data No. 1 shows a case wherein the clear preparing water W2, for example, the pure water is passed through the measuring cell 2. In that case, the preparing water W2 does not absorb the light, so that each of the absorbance values Ra, Ga, and Ba with respect to the three region component lights becomes zero. Incidentally, each of the strengths of the three region component lights measured at that time becomes a standard strength for calculating the absorbances.

Data No. 2 to 6 (hereinafter referred to as a case without the indicator) show a case wherein the first reagent A2 and the second reagent B1 excluding the selected indicators S (thymol blue and diethylene glycol) are added together to the sample water W0. In that case, the first reagent A0 and the second reagent B0 are added to the sample water W0, so that the measuring water W1 develops only the red color (the specific color) by the free residual chlorine. In the case without the indicator, each of the absorbance values Ga and Ba with respect to the G region component light and the B region component light increases as the concentration of the free residual chlorine increases.

Data No. 7 to 11 (hereinafter referred to as a case with the indicator) show a case wherein the first reagent A2 and the second reagent B1 are added together to the sample water W0. In that case, the measuring water W1 develops the red color (the specific color) by the free residual chlorine, and develops the yellow color (the first color) by the selected indicator S of the first reagent A2. In the case with the indicator, among the respective absorbance values Ra, Ga, and Ba with respect to the three region component lights, the absorbance value related to the yellow color (the first color) shows approximately a fixed value regardless of the concentration of the free residual chlorine since the concentration of the selected indicator S in the measuring water W1 is constant; however, the absorbance value related to the red color (the specific color) increases as the concentration of the free residual chlorine increases.

Data No. 12 to 16 (hereinafter referred to as a case without adding the first reagent) show a case wherein only the second reagent B1 is added without adding the first reagent A2 to the sample water W0. In that case, the first reagent A2 is a buffer solution which only indirectly relates to a color development by the dissolved substance (the free residual chlorine), so that the measuring water W1 develops the red color (the specific color) by the second reagent B1 according to the concentration of the free residual chlorine. However, this color development does not show an accurate concentration of the free residual chlorine since the first reagent A2 (the buffer solution) is not added to the sample water W0. Also, in the case without adding the first reagent, the selected indicator S is not added, so that the measuring water W1 does not develop the yellow color (the first color). In the case without adding the first reagent, each of the absorbance values Ga and Ba with respect to the G region component light and the B region component light increases as the concentration of the free residual chlorine increases.

Data No. 17 to 21 (hereinafter referred to as a case without adding the second reagent) show a case wherein only the first reagent A2 is added without adding the second reagent B1 to the sample water W0. In that case, the pH value of the measuring water W1 falls within the second pH range H2, and the measuring water W1 develops the blue color (the second color) by the selected indicator S of the first reagent A2. Also, in that case, since the second reagent B1 which directly relates to the color development by the free residual chlorine is not added, the measuring water W1 does not develop the red color (the specific color). In the case without adding the second reagent, each of the absorbance values Ra, Ga, and Ba with respect to the three region component lights has approximately a fixed value regardless of the concentration of the free residual chlorine, since the concentration of the first reagent A2 (the selected indicator S) in the measuring water W1 is constant.

Here, in the case with the indicator, the measuring water W1 develops the red color (the specific color) and the yellow color (the first color) by the free residual chlorine and the selected indicator S; however, among the absorbance values Ra, Ga, and Ba calculated at that time, the absorbance value related to the yellow color (the first color) shows approximately a fixed value regardless of the concentration of the free residual chlorine, since the concentration of the selected indicator S in the measuring water W1 is constant. Although the absorbance values Ra, Ga, and Ba related to the yellow color (the first color) can be obtained even by an experiment, the absorbance values Ra, Ga, and Ba can also be obtained by subtracting each of the absorbance values Ra, Ga, and Ba in the case without the indicator from each of the absorbance values Ra, Ga, and Ba in the case with the indicator. In that case, each of the absorbance values Ra, Ga, and Ba related to the yellow color (the first color) becomes 0 to 0.02 in the absorbance value Ra; 0.04 to 0.08 in the absorbance value Ga; and 0.18 to 0.22 in the absorbance value Ba. Therefore, each of the absorbance values Ra, Ga, and Ba based on the free residual chlorine can be obtained by respectively subtracting the absorbance values Ra, Ga, and Ba related to the yellow color (the first color), i.e., the absorbance value Ra=0.01; the absorbance value Ga=0.06; and the absorbance value Ba=0.20 from each of the absorbance values Ra, Ga, and Ba based on the free residual chlorine and the selected indicator S as with the case with the indicator.

Next, a criterion formula to judge either the case with the indicator, the case without adding the first reagent, or the case without adding the second reagent by each of the absorbance values Ra, Ga, and Ba with respect to the three region component lights will be explained.

A criterion formula (1) to judge the case with the indicator wherein the first reagent A2 and the second reagent B1 are added together to the sample water W0 is shown by:

$$2Ba-Ga=0.2 \text{ to } 0.6 \quad (1)$$

using each of the absorbance values Ga and Ba with respect to the G region component light and the B region component light simultaneously obtained. Namely, if a value of the computing equation $2Ba-Ga$, wherein each of the absorbance values Ga and Ba with respect to the G region component light and the B region component light simultaneously obtained is a function, is 0.2 to 0.6, it is judged as the case with the indicator.

In the case with the indicator, since the red color (the specific color) and the yellow color (the first color) are simultaneously developed, a computing equation is considered, which can show a portion with respect to the yellow color (the first color) excluding a portion with respect to the red color (the specific color) from the absorbance values Ra, Ga, and Ba by the three region component lights, and by a value of the computing equation, whether it is the case with the indicator or not may be judged. In the case without the indicator which only develops the red color (the specific color), when a value of the computing equation $2Ba-Ga$, wherein each of the absorbance values Ga and Ba with respect to the G region component light and the B region component light simultaneously obtained is a function, is calculated, the value thereof becomes approximately zero, so that by the computing equation, the portion with respect to the red color (the specific color) regarding the absorbance can be excluded. Also, the absorbance value Ba by the B region component light shows a coloring degree to the yellow color (the first color). Therefore, $2Ba-Ga$ becomes the computing equation which can show the portion with respect to the yellow color (the first color) excluding the portion with respect to the red color (the specific color) from the absorbance values Ra, Ga, and Ba.

Then, if the value of the computing equation 2Ba−Ga is between 0.2 and 0.6, it can be judged as the case with the indicator wherein the first reagent A2 and the second reagent B1 are added to the sample water W0, and if not, it can be judged as the case without adding the first reagent or the case without adding the second reagent. Incidentally, in the experimental example, the value of the computing equation 2Ba−Ga is 0.32 to 0.37 in the case with the indicator; 0.01 to 0.08 in the case without adding the first reagent; and −0.19 to −0.25 in the case without adding the second reagent.

Incidentally, since the value of the computing equation 2Ba−Ga shows the coloring degree to the yellow color (the first color), having a large value of 2Ba−Ga means that the first reagent A2 is added to the sample water W0 in a slightly larger quantity. Therefore, an excessive addition of the first reagent A2 can be judged by the computing equation 2Ba−Ga as well.

A criterion formula (2) to judge the case without adding the second reagent wherein only the first reagent A2 is added to the sample water W0 is shown by:

$$Ra > 0.05 \qquad (2)$$

using the absorbance value Ra with respect to the R region component light.

In the case without adding the second reagent, since the measuring water W1 develops only the blue color (the second color), the absorbance value Ra with respect to the R region component light close to a complementary color of the blue color becomes a large value at a certain level. Incidentally, the absorbance value Ra with respect to the R region component light is 0.02 to 0.03 in the case with the indicator; 0.0 to 0.03 in the case without adding the first reagent; and 0.4 to 0.46 in the case without adding the second reagent. Consequently, if the absorbance value Ra with respect to the R region component light is larger than 0.05, it can be judged as the case without adding the second reagent.

Therefore, when the concentration of the free residual chlorine is measured, if the absorbance values Ra, Ga, and Ba with respect to the three region component lights satisfy the criterion formula (1), it can be found that the first reagent A2 and the second reagent B1 are added together to the sample water W0, and if the absorbance values Ra, Ga, and Ba with respect to the three region component lights do not satisfy the criterion formula (1), it can be found that one of the first reagent A2 or the second reagent B1 is not added to the sample water W0. Also, in the same manner, if the absorbance values Ra, Ga, and Ba with respect to the three region component lights satisfy the criterion formula (2), it can be found that only the first reagent A2 is added to the sample water W0, and that the second reagent B1 is not added. Furthermore, if the absorbance values Ra, Ga, and Ba with respect to the three region component lights do not satisfy the criterion formula (1) and the criterion formula (2), it can be found that the first reagent A2 is not added to the sample water W0.

Incidentally, for the selected indicator S, there can be used, for example, alizarin yellow which develops the yellow color (the first color) within the first pH range H1 having pH 10.1 or less, and develops a violet color (the second color) within the second pH range H2 having pH 12 or above.

Meanwhile, even in a case wherein the pH value of the sample water W0 is unusual, and the pH value of the measuring water W1 does not fall within the measuring pH range H0, and falls within, for example, the second pH range H2, if the first reagent and the second reagent are added properly to the sample water W0, the concentration of the specific dissolved substance is measured. However, in that case, the pH value of the measuring water W1 does not fall within the measuring pH range H0, so that the concentration of the measured dissolved substance does not become proper. Therefore, when the concentration of the dissolved substance is measured, it becomes important to judge whether the pH value of the sample water W0 is unusual or not.

Second Embodiment

Next, the method for automatically measuring concentration of a dissolved substance according to another embodiment of the present invention will be explained with reference to FIG. 6 to FIG. 8. In this method, especially, there are judged the presence or absence of the addition of the reagent, and the presence or absence of an unusual pH value of the sample water W0.

Figure 6:
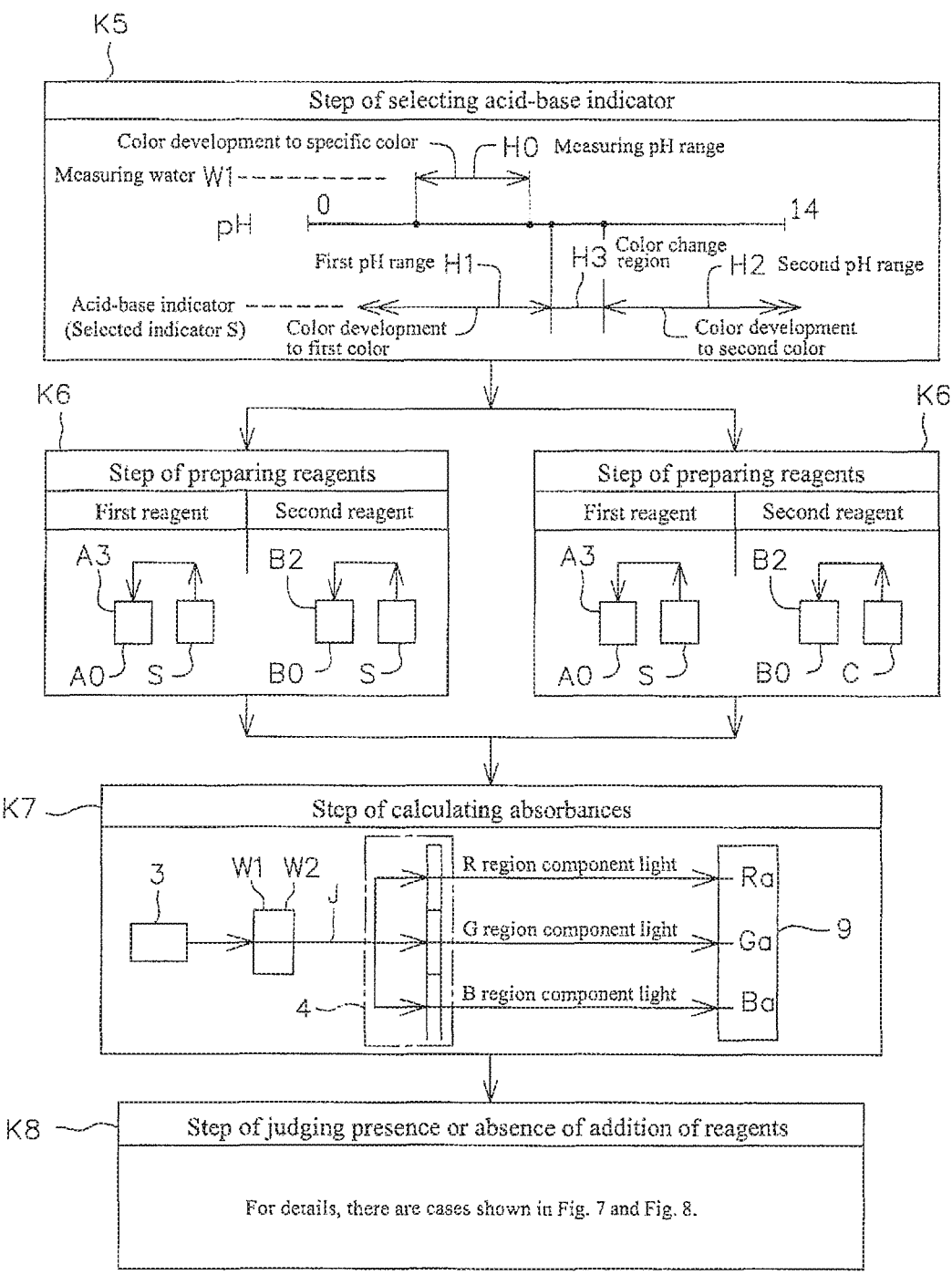
FIG. 6 is a flowchart showing the method for automatically measuring concentration of a dissolved substance according to another embodiment of the present invention.

The method for automatically measuring concentration of a dissolved substance includes the step of making the measuring water, the step of calculating the concentration of the dissolved substance, and the like, and as the characteristic steps, as shown in FIG. 6 to FIG. 8, includes a step K5 of selecting the acid-base indicator; a step K6 of preparing the reagents; a step K7 of calculating the absorbances; and a step K8 of judging the presence or absence of the addition of the reagent. Incidentally, for the concentration measuring apparatus 1, the same apparatus explained in the first embodiment is used so as to omit an explanation thereof here. Also, elements having the same functions as those explained in the first embodiment are designated by the same reference symbols, and explanations thereof are omitted.

As shown in FIG. 6, the step K5 of selecting the acid-base indicator is the same as the step K1 of selecting the acid-base indicator. Namely, in the step K5 of selecting the acid-base indicator, among acid-base indicators developing the first color within the first pH range H1 including the measuring pH range H0 where the concentration of the specific dissolved substance is measured, and developing the second color different from the first color within the second pH range H2 deviating from the first pH range H1, an acid-base indicator is selected, wherein the first color and the second color are different from the specific color by the dissolved substance. Incidentally, the selected acid-base indicator is referred to as the selected indicator S.

In the step K6 of preparing the reagents, the reagent is prepared by adding the selected indicator S to one of the first reagent A0 or the second reagent B0, and adding the selected indicator S or a coloring agent C to the other of the first reagent A0 and the second reagent B0. As shown in FIG. 6, in the step K6 of preparing the reagents, there are a case of making a first reagent A3 and a second reagent B2 by respectively adding the selected indicator S in a proper quantity to the first reagent A0 and the second reagent B0, and a case of making the first reagent A3 by adding the selected indicator S in a proper quantity to the first reagent A0, and making the second reagent B2 by adding the coloring agent C, developing the same color as the first color wherein the selected indicator S develops within the measuring pH range H0, in a proper quantity to the second reagent B0. Incidentally, the coloring agent C is used for a case wherein the selected indicator S cannot be used, and develops the first color in the measuring water W1 with no relation to the pH value.

In the step K7 of calculating the absorbance, each of the absorbances with respect to the three region component lights is calculated using the measuring water W1 wherein the prepared first reagent A3 and second reagent B2 are added together to the sample water W0. The step K3 of calculating the absorbances has been described in detail in the explanation of the concentration measuring apparatus 1 so as to omit a detailed explanation here.

In the step K8 of judging the presence or absence of the addition of the reagent, depending on whether or not the measuring water W1 develops the first color deeply (strongly), a judgement whether the first reagent A3 and the second reagent B2 are added together or not is carried out. Also, in the step K8 of judging the presence or absence of the addition of the reagent, depending on whether or not the measuring water W1 develops the second color deeply (strongly) under certain conditions, or whether or not the measuring water W1 develops the second color, a judgement whether the pH value of the sample water W0 is unusual or not is carried out. In the step K8 of judging the presence or absence of the addition of the reagent, contents have a difference between the case wherein the first reagent A3 and the second reagent B2 are made by adding only the selected indicator S (the case shown in FIG. 7), and the case wherein the first reagent A3 and the second reagent B2 are made by adding the selected indicator S and the coloring agent C (the case shown in FIG. 8).

FIG. 7 shows the step K8 of judging the presence or absence of the addition of the reagent in the case wherein the first reagent A3 and the second reagent B2 are made by adding the selected indicator S respectively to the first reagent A0 and the second reagent B0.

When the first reagent A3 and the second reagent B2 are added together to the sample water W0, the measuring water W1 develops the specific color by the specific dissolved substance in the sample water W0, and develops the first color deeply (strongly) by the selected indicators S in the first reagent A3 and the second reagent B2. Also, when only one of the first reagent A3 or the second reagent B2 is added to the sample water W0, in the case wherein the pH value of the measuring water W1 is within the first pH range H1, the measuring water W1 develops the first color; in the case wherein the pH value of the measuring water W1 is within the second pH range H2, the measuring water W1 develops the second color; and in the case wherein the pH value of the measuring water W1 is within a color change region, the measuring water W1 develops an intermediate color between the first color and the second color.

Namely, in the case wherein the first reagent A3 and the second reagent B2 are added together, the measuring water W1 develops the first color deeply (strongly); however in the case wherein only one of the first reagent A3 or the second reagent B2 is added, although the measuring water W1 sometimes develops the first color, the measuring water W1 does not develop the first color deeply (strongly). Therefore, if the measuring water W1 develops the first color deeply (strongly), it is judged that the first reagent A3 and the second reagent B2 are added together, and if the measuring water W1 does not develop the first color deeply (strongly), it is judged that only one of the first reagent A3 or the second reagent B2 is added. Incidentally, even in the case wherein the pH value of the sample water W0 is unusual, the measuring water W1 does not develop the first color deeply (strongly).

On the other hand, even if the first reagent A3 and the second reagent B2 are added together, since the pH value of the sample water W0 is unusual, when the pH value of the measuring water W1 falls within the second pH range H2, the measuring water W1 develops the specific color by the specific dissolved substance in the sample water W0, and develops the second color deeply (strongly) by the selected indicators S in the first reagent A3 and the second reagent B2. Also, only when the pH value of the sample water W0 is unusual, the measuring water W1 develops the second color deeply (strongly). Therefore, if the measuring water W1 develops the second color deeply (strongly), it is judged that the pH value of the sample water W0 is unusual. In that case, the measuring water W1 develops the specific color by the specific dissolved substance; however, since the pH value of the measuring water W1 is not proper, the concentration of the measured dissolved substance does not become a proper value.

FIG. 8 shows the step K8 of judging the presence or absence of the addition of the reagent in a case wherein the first reagent A3 is made by adding the selected indicator S to the first reagent A0, and the second reagent B2 is made by adding the coloring agent C to the second reagent B0.

In that case, when the first reagent A3 and the second reagent B2 are added together to the sample water W0, the measuring water W1 develops the specific color by the specific dissolved substance in the sample water W0, and develops the first color deeply (strongly) by the selected indicator S in the first reagent A3 and the coloring agent C in the second reagent B2. Also, when only one of the first reagent A3 or the second reagent B2 is added to the sample water W0, in the case wherein the pH value of the measuring water W1 is within the first range H1, the measuring water W1 develops the first color by the selected indicator S in the first reagent A3 or the coloring agent C in the second reagent B2, and in the case wherein the pH value of the measuring water W1 is within the second range H2, the measuring water W1 develops the second color by the selected indicator S in the first reagent A3, or develops the first color by the coloring agent C in the second reagent B2. Furthermore, in the case wherein the pH value of the measuring water W1 is within the color change region, the measuring water W1 develops the intermediate color between the first color and the second color by the selected indicator S in the first reagent A3, or develops the first color by the coloring agent C in the second reagent B2.

Therefore, even in that case, if the measuring water W1 develops the first color deeply (strongly), it is judged that the first reagent A3 and the second reagent B2 are added together, and if the measuring water W1 does not develop the first color deeply (strongly), it is judged that only one of the first reagent A3 or the second reagent B2 is added. Incidentally, even in the case wherein the pH value of the sample water W0 is unusual, the measuring water W1 does not develop the first color deeply (strongly).

On the other hand, in the case wherein the pH value of the measuring water W1 wherein only the first reagent is added to the sample water W0 is within the first pH range H1, the measuring water W1 wherein one or both of the first reagent or/and the second reagent is/are added to the sample water W0 does not develop the second color by the selected indicator S. However, even in such a case, since the pH value of the sample water W0 is unusual, if the pH value of the measuring water W1 falls within the second pH range H2, the measuring water W1 develops the second color. Namely, if the measuring water W1 wherein the first reagent A3 and the second reagent B2 are added together to the sample water W0 develops the second color, the pH value of the sample water W0 is judged to be unusual. Also, if the measuring water W1 wherein only the first reagent is added to the sample water W0 develops the second color, the pH value of the sample water W0 is judged to be unusual as well.

Here, whether or not the measuring water W1 is developing the first color or the second color deeply (strongly), or whether or not the measuring water W1 is developing the second color can be judged by respectively considering a computing equation, wherein any of each of the absorbance values Ra, Ga, and Ba with respect to the three region component lights is a function, so as to judge whether or not a value of the aforementioned computing equation falls within a specific range. A specific example of the computing equation will be explained in the later-described experimental example.

As mentioned above, in the method for automatically measuring concentration of a dissolved substance, the presence or absence of the addition of the first reagent A3 and the second reagent B2 relative to the sample water W0 can be judged reliably only by adding the selected indicator S to one of the first reagent A0 or the second reagent B0, and adding the selected indicator S or the coloring agent C to the other of the first reagent A0 or the second reagent B0. Therefore, the method for automatically measuring concentration of a dissolved substance does not require the large cost in order to judge the presence or absence of the addition of the reagent as well. Also, in the method for automatically measuring concentration of a dissolved substance, it is sufficient that the light emitting device and the light receiving device are a set, so that the highly reliable judgment regarding the presence or absence of the addition of the reagent can be carried out without complicating the apparatus. Furthermore, in the method for automatically measuring concentration of a dissolved substance, even in the case wherein the pH value of the sample water is unusual, this can be reliably judged under certain conditions, so that the occurrence of an error of the measurement of the concentration of the dissolved substance resulting from the unusual pH value of the sample water can be prevented.

Incidentally, the computing processing apparatus 9 additionally has a function of judging the presence or absence of the addition of the first reagent A3 and the second reagent B2, and a function of judging the presence or absence of the unusual pH value of the sample water W0, so that the judgement of the presence or absence of the addition of the reagent and the judgement of the presence or absence of the unusual pH value of the sample water W0 are automatically carried out by the concentration measuring apparatus 1.

Also, as explained in the first embodiment, each of the absorbance values Ra, Ga, and Ba of the measuring water W1 developing the specific color which becomes necessary for calculating the concentration of the specific dissolved substance can be obtained by subtracting each of the absorbance values Ra, Ga, and Ba with respect to the first color from each of the absorbance values Ra, Ga, and Ba of the measuring water W1 developing the specific color and the first color.

FIG. 9 and FIG. 10 show data of an experimental example for investigating the presence or absence of the addition of the reagent.

This experimental example relates to the concentration measurement of phosphate ion, and as for the first reagent A0, there is used ascorbic acid, and as for the second reagent B0, there is used a mixture solution of ammonium molybdate, sulfuric acid, and antimonyl potassium tartarate. An ascorbic acid solution gradually oxidizes and has a short storage period as the reagent so as to be treated as another reagent. The measuring water W1 wherein the first reagent A0 and the second reagent B0 are added together to the sample water W0 including the phosphate ion is maintained in the measuring pH range H0 wherein the pH is 6.8 or less, and develops the blue color (the specific color) by the phosphate ion. For the selected indicator S, there is used phenol red. The phenol red develops the yellow color (the first color) in pH<6.8 which is in the first pH range H1, and develops the red color (the second color) in pH>8.4 which is the second pH range H2. For the coloring agent C, there is used tartrazine. The tartrazine develops the yellow color same as the first color wherein the selected indicator S develops in the measuring pH range H0 regardless of the pH value.

Then, as for the reagent after the preparation, there are used the first reagent A3 wherein the selected indicator S in a proper quantity is added to the first reagent A0, and the second reagent B2 wherein the coloring agent C in a proper quantity is added to the second reagent B0. Incidentally, the second reagent B0 has very high acidity, and a difficulty in stability, so that for the second reagent B0, instead of the selected indicator S, the coloring agent C is used.

The sample water W0 is prepared by dissolving sodium phosphate to a pure water so that the concentration of phosphate ion becomes 0.0 to 5.0 mg/L. The measuring water W1 is made by adding each 0.2 mL of the first reagent A3 and the second reagent B2 to 10 mL of the sample water W0. Here, in Data No. 2 to 25, the pH value of the sample water W0 shows near 7, and the first reagent A3 and the second reagent B2 show acidity, so that the pH value of the measuring water W1, wherein only one of the first reagent A3 or the second reagent B2 is added to the sample water W0, inevitably acidifies so as to belong to the first pH range H1. Also, sodium hydroxide is added to the sample water W0 in Data No. 26 to 31 so that the pH value thereof becomes unusually high, and the pH value of the measuring water W1 wherein the second reagent B2 is added to the sample water W0 is prepared to fall within the second pH range H2. Moreover, excessive sodium hydroxide is added further to the sample water W0 in Data No. 32 to 37, and the pH value of the measuring water W1 wherein the first reagent A3 and the second reagent B2 are added together to the measuring water W1 is prepared to fall within the second pH range H2. Incidentally, the measurement of the concentration of the phosphate ion is carried out according to molybdenum blue (ascorbic acid reduction) absorptiometry of JIS analysis method.

In FIG. 9, Data No. 1 shows the case wherein the clear preparing water W2, for example, the pure water is passed through the measuring cell 2.

Data No. 2 to 7 (hereinafter referred to as a case without the coloring agent) show a case wherein the first reagent A3 and the second reagent B2, i.e., the first reagent A0 and the second reagent B0 excluding the coloring agent C and the selected indicator S are added to the sample water W0. In that case, the measuring water W1 develops only the blue color (the specific color) by the phosphate ion. In the case without the coloring agent, the absorbance values Ra, Ga, and Ba with respect to the three region component lights increase as the concentration of the phosphate ion increases.

Data No. 8 to 13 (hereinafter referred to as a case with the coloring agent) show a case wherein the first reagent A3 and the second reagent B2 are added together to the sample water W0. In that case, the measuring water W1 develops the blue color (the specific color) by the phosphate ion, and develops the yellow color (the first color) deeply (strongly) by the selected indicator S of the first reagent A3 and the coloring agent C of the second reagent B2. In the case with the coloring agent, among the respective absorbance values Ra, Ga, and Ba with respect to the three region component lights, the absorbance value related to the yellow color (the first color) has the constant concentration of the coloring agent C and the selected indicator S in the measuring water W1 so as to show approximately a fixed value regardless of the concentration of the phosphate ion; however, the absorbance value related to the blue color (the specific color) increases as the concentration of the phosphate ion increases.

Data No. 14 to 19 (hereinafter referred to as a case without adding the second reagent) show a case wherein only the first reagent A3 is added without adding the second reagent B2 to the sample water W0. In that case, the measuring water W1 develops the yellow color (the first color) by the selected indicator S of the first reagent A3; however, since the second reagent B2 is not added, the measuring water W1 does not develop the blue color (the specific color). In the case without adding the second reagent, the concentration of the selected indicator S in the measuring water W1 is constant, so that the absorbance value Ba and the like with respect to the B region component light become a fixed value.

Data No. 20 to 25 (hereinafter referred to as a case without adding the first reagent) show a case wherein only the second reagent B2 is added to the sample water W0. In that case, the measuring water W1 develops the yellow color (the first color) by the coloring agent C of the second reagent B2; however, since the first reagent A3 is not added, the measuring water W1 does not develop the blue color (the specific color). In the case without adding the first reagent, the concentration of the coloring agent C in the measuring water W1 is constant, so that the absorbance value Ba and the like with respect to the B region component light become a fixed value.

Data No. 26 to 31 (hereinafter referred to as an alkaline case without adding the second reagent) show a case wherein only the first reagent A3 is added to the sample water W0 having an unusually high pH value. In that case, the pH value of the measuring water W1 falls within the second pH range H2, so that the measuring water W1 develops the red color (the second color) by the selected indicator S. In the alkaline case without adding the second reagent, the concentration of the selected indicator S in the measuring water W1 is constant, so that the respective absorbance values Ra, Ga, and Ba with respect to the three region component lights become approximately a fixed value regardless of the concentration of the phosphate ion.

Data No. 32 to 37 (hereinafter referred to as an alkaline case with the coloring agent) show a case wherein the first reagent A3 and the second reagent B2 are added together to the sample water W0 having the unusually high pH value. In that case, the pH value of the measuring water W1 falls within the second pH range H2, so that the measuring water W1 develops the blue color (the specific color) by the phosphate ion; develops the red color (the second color) by the selected indicator S of the first reagent A3; and develops the yellow color (the first color) by the coloring agent C of the second reagent B2. In the alkaline case with the coloring agent, among the respective absorbance values Ra, Ga, and Ba with respect to the three region component lights, the absorbance values related to the yellow color (the first color) and the red color (the second color) show approximately a fixed value regardless of the concentration of the phosphate ion since the concentration of the coloring agent C and the selected indicator S in the measuring water W1 is constant; however, the absorbance value related to the blue color (the specific color) increases as the concentration of the phosphate ion increases.

Next, criterion formulas to judge whether or not it is the case with the coloring agent, or whether or not the pH value of the sample water W0 is unusually high by the respective absorbance values Ra, Ga, and Ba with respect to the three region component lights will be explained.

A criterion formula (3) to judge the case with the coloring agent wherein the first reagent A3 and the second reagent B2 are added together to the sample water W0 is shown by:

$$Ba - 0.34 Ra > 0.15 \qquad (3)$$

using each of the absorbance values Ra and Ba with respect to the R region component light and the B region component light simultaneously obtained. Namely, if a value of the computing equation Ba−0.34 Ra, wherein each of the absorbance values Ra and Ba with respect to the R region component light and the B region component light simultaneously obtained is a function, is larger than 0.15, it is judged as the case with the coloring agent.

In the case with the coloring agent, since the blue color (the specific color) and the yellow color (the first color) are simultaneously developed, a computing equation of the absorbance is considered, which can show a portion with respect to the yellow color (the first color) excluding a portion with respect to the blue color (the specific color) from the absorbance values Ra, Ga, and Ba with respect to the three region component lights, and by a value of the computing equation, whether it is the case with the coloring agent or not may be judged. In the case without the coloring agent which only develops the blue color (the specific color), when a value of the computing equation Ba−0.34 Ra is calculated, the value thereof becomes approximately zero (0), so that by the computing equation, the portion with respect to the blue color (the specific color) regarding the absorbance can be excluded. Also, the absorbance value Ba with respect to the B region component light shows a coloring degree to the yellow color (the first color). Therefore, the computing equation Ba−0.34 Ra becomes the computing equation which can show the coloring degree to the yellow color (the first color) excluding the portion with respect to the blue color (the specific color) from the absorbance values Ra, Ga, and Ba.

On the other hand, in the case with the coloring agent, compared to the case without adding the second reagent or the case without adding the first reagent, the yellow color (the first color) is developed deeply (strongly). Therefore, if the value of the computing equation Ba−0.34 Ra is larger than 0.15, it can be judged as the case with the coloring agent wherein the first reagent A3 and the second reagent B2 are added together to the sample water W0, and if not, it can be judged as the case without adding the first reagent, the case without adding the second reagent, or the like. Incidentally, in the experimental example, the value of the computing equation Ba−0.34 Ra is 0.17 in the case with the coloring agent; 0.1 in the case without adding the second reagent; 0.08 in the case without adding the first reagent; 0.02 to 0.04 in the alkaline case without adding the second reagent; and 0.11 in the alkaline case with the coloring agent.

A criterion formula (4) to judge whether the pH value of the sample water W0 is unusually high by the color development to the second color in the measuring water W1 is shown by:

$$Ga - 0.66 Ra > 0.1 \qquad (4)$$

using the respective absorbance values Ra and Ga with respect to the R region component light and the G region component light. Namely, if a value of the computing equation Ga−0.66 Ra, wherein each of the absorbance values Ra and Ga with respect to the R region component light and the G region component light simultaneously obtained is a function, is larger than 0.1, it is judged as the unusually high pH value of the sample water W0. In that case, it is premised that the measuring water W1 wherein only one of the first reagent A3 or the second reagent B2 is added to the sample water W0 without the unusual pH value does not have a pH value thereof within the second pH range H2, and does not develop the second color.

In the alkaline case without adding the second reagent, the measuring water W1 develops only the red color (the second color), and in the alkaline case with the coloring agent, the measuring water W1 develops the blue color (the specific color), the yellow color (the first color), and the red color (the second color). Also, without the unusual pH value of the sample water W0, in the case with the coloring agent, the case without adding the second reagent, and the case without adding the first reagent, the measuring water W1 does not develop the red color (the second color). Therefore, if the color development to the red color (the second color) in the measuring water W1 is detected, it can be found that the pH value of the sample water W0 is unusual.

On the other hand, in the case without the coloring agent which develops only the blue color (the specific color), when the value of the computing equation Ga−0.66 Ra, wherein each of the absorbance values Ra and Ga with respect to the R region component light and the G region component light simultaneously obtained is a function, is calculated, the value thereof becomes approximately zero (0), so that by the computing equation, the portion with respect to the blue color (the specific color) regarding the absorbance can be excluded. Also, the absorbance value Ga by the G region component light shows a coloring degree to the red color (the second color). Therefore, the computing equation Ga−0.66 Ra becomes the computing equation which can show the coloring degree to the red color (the second color) excluding the portion with respect to the blue color (the specific color) from the absorbance values Ra, Ga, and Ba with respect to the three region component lights. Then, if the value of the computing equation Ga−0.66 Ra is larger than 0.1, the pH value of the sample water W0 can be judged to be unusually high. Incidentally, in the experimental example, the value of the computing equation Ga−0.66 Ra is 0.05 to 0.06 in the case with the coloring agent; 0.01 in the case without adding the second reagent; 0.0 to 0.01 in the case without adding the first reagent; 0.43 to 0.44 in the alkaline case without adding the second reagent; and 0.42 to 0.44 in the alkaline case with the coloring agent.

Therefore, when the concentration of the phosphate ion is measured, if the respective absorbance values Ra, Ga, and Ba with respect to the three region component lights satisfy the criterion formula (3), it can be found that the first reagent A3 and the second reagent B2 are added together to the sample water W0 having a proper pH value, and if the absorbance values Ra, Ga, and Ba with respect to the three region component lights do not satisfy the criterion formula (3), for example, it can be found that one of the first reagent A3 or the second reagent B2 is not added. Also, when the concentration of the phosphate ion is measured, if the respective absorbance values Ra, Ga, and Ba with respect to the three region component lights satisfy the criterion formula (4) under certain conditions, it can be found that the pH value of the sample water W0 is unusual.

Incidentally, in the experimental example, a case wherein the first reagent A3 and the second reagent B2 are made by adding only the selected indicator S to the first reagent A0 and the second reagent B0 has not been explained. However, even in that case, a judgement whether the first reagent A3 and the second reagent B2 are added together to the sample water W0 or not can be carried out using the criterion formula (3). Also, in that case, although the measuring water W1 sometimes develops the second color deeply (strongly) by the unusual pH value of the sample water W0, whether or not the pH value of the sample water W0 at that time is unusual can be judged using the computing equation wherein any of the absorbances of the three region component lights is a function.

Also, the computing equation of the criterion formula (4) may be shown with the absorbance value Ga with respect to the G region component light close to a complementary color of the red color (the second color), and if the absorbance value Ga is larger than a specific value, the pH value of the sample water W0 can be judged to be unusually high.

Furthermore, even in a case wherein the concentration of the specific dissolved substance is measured by adding one reagent to the sample water W0, whether the pH value of the sample water W0 is unusual or not can be judged in the same manner by adding the selected indicator S to the aforementioned reagent.

EXPLANATION OF SYMBOLS

A0, A1, A2, and A3 first reagents
B0, B1, and B2 second reagents
C a coloring agent
H0 a measuring pH range (a specific pH range)
H1 a first pH range (a first pH range)
H2 a second pH range (a second pH range)
P1 and P2 pH regulators
Ra an absorbance value with respect to a red region component light
Ga an absorbance value with respect to a green region component light
Ba an absorbance value with respect to a blue region component light
S a selected indicator (a selected acid-base indicator)
T a reagent added water
W0 a sample water
W1 a measuring water

What is claimed is:
1. A method for automatically measuring concentration of a dissolved substance, comprising:
   a step of making a measuring water by adding individually a first prepared reagent and a second prepared reagent to a sample water sampled from a target water system, wherein the first prepared reagent and the second prepared reagent comprise respectively a first reagent and a second reagent selected such that the measuring water develops a specific color by interaction of the first reagent and the second reagent with the dissolved substance if a pH value of the measuring water is kept in a specific pH range;
   a step of selecting one acid-base indicator which develops respectively different colors other than the specific color in a first pH range including the specific pH range, and a second pH range deviating from the first pH range;
   a step of preparing the first prepared reagent and the second prepared reagent, wherein, in a case wherein one of pH values of first and second reagent added waters is within the second pH range, one of the first and second prepared reagents is prepared by adding the acid-base indicator selected to one of the first reagent and the second reagent of which the reagent added water is on a side within the second pH range, and the other of the first and second prepared reagents is the other of the first and second reagents, and in a case wherein neither of the pH values of the first and second reagent added waters is within the second pH range, the one of the first and second prepared reagents is prepared by adding the acid-base indicator selected and a pH regulator for making the pH value of the respective reagent added water within the second pH range to the one of the first and second reagents of which the respective reagent added water has the pH value on a side close to the second pH range, and the other of the first and second prepared reagents is prepared by adding another pH regulator for neutralizing the pH regulator added to the one reagent to the other of the first and second reagents, wherein the first reagent added water is obtained by adding the first reagent to the sample water and the second reagent added water is obtained by adding the second reagent to the sample water;

a step of irradiating a white light to the measuring water;

a step of calculating each of absorbances with respect to a red region component light, a green region component light, and a blue region component light which are obtained by dividing a light in a visible light region of the white light transmitted through the measuring water into nearly three parts;

a step of judging presence or absence of addition of both of the first reagent and the second reagent in the sample water by using a first calculated absorbance; and a step of calculating concentration of the dissolved substance in the sample water by using a second calculated absorbance.

2. A method for automatically measuring concentration of a dissolved substance, comprising:

a step of making a measuring water by adding individually a first prepared reagent and a second prepared reagent to a sample water sampled from a target water system, wherein the first prepared reagent and the second prepared reagent comprise respectively a first reagent and a second reagent selected such that the measuring water develops a specific color by interaction of the first reagent and the second reagent with the dissolved substance if a pH value of the measuring water is kept in a specific pH range;

a step of selecting one acid-base indicator which develops respectively different colors other than the specific color in a first pH range including the specific pH range, and a second pH range deviating from the first pH range;

a step of preparing the first prepared reagent and the second prepared reagent by adding the acid-base indicator selected to one reagent of the first reagent and the second reagent, and by adding the acid-base indicator selected or a coloring agent for developing the same color that the acid-base indicator selected develops in the first pH range to the other reagent of the first reagent and the second reagent;

a step of irradiating a white light to the measuring water:

a step of calculating each of absorbances with respect to a red region component light, a green region component light, and a blue region component light which are obtained by dividing a light in a visible light region of the white light transmitted through the measuring water into nearly three parts;

a step of judging presence or absence of addition of both of the first reagent and the second reagent in the sample water and whether a pH value of the sample water is unusual such that the pH value of the measuring water is in the second pH range by using a first calculated absorbance; and a step of calculating concentration of the dissolved substance in the sample water by using a second calculated absorbance.

* * * * *